(12) United States Patent
Tanter et al.

(10) Patent No.: US 10,955,535 B2
(45) Date of Patent: Mar. 23, 2021

(54) ACOUSTIC IMAGING METHOD AND DEVICE FOR DETECTING LINEARLY COMBINED REVERBERATED WAVES VIA DECODING MATRICES

(71) Applicants: CENTRE NATIONAL DE LA RE-CHERCHE SCIENTIFIQUE—CNRS, Paris (FR); INSERM (INSTITUT NATIONAL DE LA SANTÉ ET DE LA RECHERCHE MÉDICALE), Paris (FR)

(72) Inventors: Mickaël Tanter, Bagneux (FR); Bruno-Félix Osmanski, Paris (FR); Mathieu Pernot, Paris (FR); Jean-Luc Gennisson, Cergy (FR)

(73) Assignees: CENTRE NATIONAL DE LA RECHERCHE SCIENTIFIQUE (CNRS), Paris (FR); INSERM, Paris (FR)

( * ) Notice: Subject to any disclaimer, the term of this patent is extended or adjusted under 35 U.S.C. 154(b) by 1012 days.

(21) Appl. No.: 15/512,377

(22) PCT Filed: Sep. 25, 2015

(86) PCT No.: PCT/FR2015/052566
§ 371 (c)(1),
(2) Date: Mar. 17, 2017

(87) PCT Pub. No.: WO2016/046506
PCT Pub. Date: Mar. 31, 2016

(65) Prior Publication Data
US 2017/0276775 A1 Sep. 28, 2017

(30) Foreign Application Priority Data

Sep. 26, 2014 (FR) ...................... 14 59136

(51) Int. Cl.
*G01S 7/52* (2006.01)
*A61B 8/00* (2006.01)
(Continued)

(52) U.S. Cl.
CPC ........ *G01S 7/52046* (2013.01); *A61B 8/4477* (2013.01); *A61B 8/5207* (2013.01); *G01S 15/8959* (2013.01); *G01S 15/8977* (2013.01)

(58) Field of Classification Search
CPC ............. G01S 7/52046; G01S 15/8959; G01S 15/8977; A61B 8/4477; A61B 8/5207
See application file for complete search history.

(56) References Cited

U.S. PATENT DOCUMENTS 5,851,187 A 12/1998 Thomas, III
6,005,916 A * 12/1999 Johnson .................. A61B 5/05
378/87

(Continued)

FOREIGN PATENT DOCUMENTS

WO WO 2013/069752 A1 5/2013

OTHER PUBLICATIONS

Chiao R Y et al: "Sparse array imaging with spatially-encoded transmits", Ultrasonics Sumposium, 1997. Proceedings., 1997 IEEE Toronto, Ont., Canada Oct. 5-8, 1997, New York, NY, USA, IEEE, US, vol. 2, Oct. 5, 1997 (Oct. 5, 1997), pp. 1679-1682, XP010271620, DOI: 10.1109/ULTSYM.1997.663318 ISBN: 978-0-7803-4153-01 abrégé; figures 3-7 chapitre 2. "Hadamard spatial cooding" Chapitre 3 "Results and discussion" chapitre 4. "Conclusion".

(Continued)

*Primary Examiner* — Serkan Akar
(74) *Attorney, Agent, or Firm* — Osha Bergman Watanabe & Burton LLP (57) ABSTRACT

According to the invention, n incident acoustic waves Ei(t), obtained by linearly combining n elemental incident waves
(Continued)

E0$i$(t) with an encoding matrix Hc are consecutively transmitted in a medium to be imaged. n reverberated waves Ri(t) from the medium to be imaged are then consecutively detected, following the transmission of the n incident waves; then n elemental reverberated waves R0$i$(t) are determined by linearly combining the detected n reverberated waves Ri(t) with a decoding matrix Hd. The Hc and Hd matrices are such that Hc·Hd=D, where D is a diagonal matrix of order n, all the diagonal elements of which are greater than 1.

8 Claims, 4 Drawing Sheets

(51) Int. Cl.
*A61B 8/08* (2006.01)
*G01S 15/89* (2006.01)

(56) References Cited

U.S. PATENT DOCUMENTS

| | | | |
|---|---|---|---|
| 6,048,315 A | | 4/2000 | Chiao |
| 2006/0287596 A1* | | 12/2006 | Johnson .................. A61B 8/14 600/437 |
| 2014/0024943 A1* | | 1/2014 | Nicolas .................... A61B 8/54 600/447 |
| 2014/0243679 A1* | | 8/2014 | Thomas, III ........ G01S 15/8915 600/463 |
| 2016/0061950 A1* | | 3/2016 | Xu ...................... G01S 15/8997 342/25 A |

OTHER PUBLICATIONS

Svetoslav I Nikolov and Jorgen A Jensen: "Comparison Between Dierent Encoding Schemes for Synthetic Aperture Imaging" Progress in Biomedical Optics and Imaging, SPIR—International Society for Optical Engineering, Bellingham, WA, US, vol. 4687, Jan. 1, 2002 (Jan. 1, 2002), pp. 1-12, XP007906293, ISSN: 1605-7422 ISBN: 978-1-62841-502-5 abrégé; figures 3b, 4 chapitre, 2.3.2 "Spatial encoding" chapitre 3. "Results" and 4. "Conclusions".

Montaldo G et al: "Coherent plane-wave compounding for very high frame rate ultrasonography and transient elastography", IEEE Transactions on Ultrasonics, Ferroelectrics and Frequency Control, IEEE, US, vol. 56, No. 3, Mar. 1, 2009 (Mar. 1, 2009), pp. 489-506, XP011255897, ISSN: 0885-3010 cité dans la demande le document en entire.

International Search Report for related Application No. PCT/FR2015/052566 reported on Nov. 24, 2015.

* cited by examiner

ACOUSTIC IMAGING METHOD AND DEVICE FOR DETECTING LINEARLY COMBINED REVERBERATED WAVES VIA DECODING MATRICES

CROSS-REFERENCE TO RELATED APPLICATION

This Application is a 35 USC § 371 US National Stage filing of International Application No. PCT/FR2015/052566 filed on Sep. 25, 2015, and claims priority under the Paris Convention to French Patent Application No. 14 59136 filed on Sep. 26, 2014.

FIELD OF THE DISCLOSURE

The invention relates to acoustic imaging methods and devices.

BACKGROUND OF THE DISCLOSURE

Document EP2101191 and the article by Montaldo et al. entitled "Coherent plane-wave compounding for very high frame rate ultrasonography and transient elastography" (IEEE Trans Ultrason Ferroelectr Freq Control 2009 March; 56(3): 489-506) describe an acoustic imaging method in which an array of acoustic transducers successively transmits a series of n incident acoustic waves $E_i(t)$, plane or diverging, in a medium to be imaged, the n incident waves being propagated in the medium to be imaged and respectively generating n reverberated waves, and the transducer array detects signals representative of the reverberated waves.

SUMMARY OF THE DISCLOSURE

This method has enabled considerable progress in terms of image acquisition speed and image definition.

However, methods of this type have the disadvantage that the resolution of the obtained images decreases rapidly with depth due to attenuation of the ultrasound waves in the medium to be imaged, in particular biological tissues.

One solution to this problem is to increase the amplitude of the ultrasound waves transmitted. However, this magnitude cannot be increased beyond certain thresholds dictated by the ultrasonic transducers and/or the electronics controlling the transducers and/or the safety standards in effect concerning medical applications.

Other solutions based on temporal or spatial encoding of the transmitted signals have been proposed, but these solutions require the use of complex and costly transmission electronics, which in practice cannot be used in conventional ultrasound imaging devices.

The present invention is intended to overcome these disadvantages and provide an acoustic imaging method enabling improved resolution without loss of imaging speed, without significantly increasing the complexity or cost of the acoustic imaging devices in which it is implemented.

To this end, the present invention proposes an ultrasound imaging method comprising the following steps:

(a) a transmission/reception step during which an array of acoustic transducers successively transmits a series of n incident acoustic waves $E_i(t)$ in an area of observation that is part of a medium to be imaged, and the array of acoustic transducers detects reverberated waves $R_i(t)$ which are respectively reverberated by the medium to be imaged following the transmission of the n incident waves, where n is a natural number at least equal to 2, said incident acoustic waves being obtained by linearly combining n elemental incident waves $E0_i(t)$ in a manner corresponding to the formula:

$$\vec{E}(t) = H_c \cdot \vec{E}0(t) \quad (1)$$

where:

$H_c$ is a square matrix of order n (referred to as the encoding matrix), $\vec{E}(t) = [E_i(t)]$ is a vector having the n incident waves as components, $\vec{E}0(t) = [E0_i(t)]$ is a vector having the n elemental incident waves as components, said elemental incident waves being plane waves or diverging waves or waves focused at different points in space respectively having n different wavefronts, each elemental incident wave being transmitted by a plurality of acoustic transducers of the array of acoustic transducers and sweeping the entire area of observation, (b) a decoding step during which n elemental reverberated waves $R0_i(t)$ are determined by linearly combining the n reverberated waves $R_i(t)$ detected, corresponding to the formula:

$$\vec{R}0(t) = \lambda \cdot H_d \cdot \vec{R}(t) \quad (2)$$

where:

$\lambda$ is a non-zero constant, $H_d$ is a square matrix of order n (referred to as the decoding matrix), matrices $H_c$ and $H_d$ being such that $Hc \cdot Hd = D$ where $D$ is a diagonal matrix of order n in which all diagonal elements $d_{ii}$ are non-zero, $\vec{R}(t) = [R_i(t)]$ is a vector having the n reverberated waves as components, $\vec{R}0(t) = [R0_i(t)]$ is a vector having the n elemental reverberated waves as components, (c) an image construction step during which a synthetic image is produced from the n elemental reverberated waves $R0_i(t)$.

The invention thus can significantly increase the resolution of the ultrasound images obtained, without needing to increase the number of bursts of incident waves (and therefore without lowering the frame rate), without needing to increase the complexity of the ultrasound device, and without needing to increase the amplitude of the incident acoustic waves.

Indeed, the n elemental reverberated waves $R0_i(t)$ are respectively representative of the signals that would be obtained by separately transmitting the n elemental incident waves $E0_i(t)$ and then capturing the corresponding reverberated waves, but said n elemental reverberated waves $R0_i(t)$ have an amplitude greater than the amplitude of the signals that would be detected by separately transmitting the n elemental incident waves $E0_i(t)$, which leads to improved resolution.

This gain in amplitude and thus in resolution is due to the fact that each elemental reverberated wave $R0_i(t)$ combines information from n bursts of incident waves, and is therefore richer in information.

The invention can be used in all methods where the ultrasound image is synthesized from n bursts of plane or diverging or multifocal waves, particularly as described in document EP2101191, for example for the imaging of shear waves, the imaging of vascular networks (highly sensitive Doppler imaging or other, in particular functional imaging of the brain), etc.

In various embodiments of the method according to the invention, one or more of the following arrangements may possibly be used:

the matrices $H_c$ and $H_d$ are such that $Hc \cdot Hd = D$, where D is a diagonal matrix of order n in which all diagonal elements $d_{ii}$ are greater than 1;

n is an even non-zero natural number;

matrix Hc is a Hadamard matrix of order n and matrix $H_d$ is the transpose of matrix Hc;

each of said acoustic waves is represented by a plurality of time signals, each time signal representing said acoustic wave at a transducer that is part of said transducer array;

the method further comprises, after the decoding step, an image construction step in which a synthetic image is created from the n elemental reverberated waves $R0_i(t)$.

The invention also relates to a device for implementing a method as defined above, comprising:

(a) transmission means adapted for successively transmitting a series of n incident acoustic waves $E_i(t)$ in an area of observation within a medium to be imaged, by means of an array of acoustic transducers, said incident acoustic waves being obtained by linearly combining n elemental incident waves $E0_i(t)$ in a manner corresponding to the formula:

$$\vec{E}(t) = H_c \cdot \vec{E}0(t) \quad (1)$$

where:

$H_c$ is a square matrix of order n, $\vec{E}(t) = [E_i(t)]$ is a vector having the n incident waves as components, $\vec{E}0(t) = [E0_i(t)]$ is a vector having the n elemental incident waves as components, said elemental incident waves being plane waves or diverging waves or waves focused at different points in space respectively having n different wavefronts, each elemental incident wave being transmitted by a plurality of acoustic transducers of the array of acoustic transducers and sweeping the entire area of observation, (b) reception means, adapted for the successive detection by the array of acoustic transducers of n reverberated waves $R_i(t)$ which are respectively reverberated by the medium to be imaged following the transmission of the n incident waves, (c) decoding means adapted for determining n elemental reverberated waves $R0_i(t)$ by linearly combining the detected n reverberated waves $R_i(t)$, in a manner corresponding to the formula:

$$\vec{R}0(t) = H_d \cdot \vec{R}(t) \quad (2)$$

where:

$H_d$ is a square matrix of order n, matrices $H_c$ and $H_d$ being such that $Hc \cdot Hd = D$ where D is a diagonal matrix of order n in which all diagonal elements $d_{ii}$ are non-zero, $\vec{R}(t) = [R_i(t)]$ is a vector having the n reverberated waves as components, $\vec{R}0(t) = [R0_i(t)]$ is a vector having the n elemental reverberated waves as components, (d) image construction means adapted for creating a synthetic image from the n elemental reverberated waves $R0_i(t)$.

BRIEF DESCRIPTION OF DRAWINGS

Other features and advantages of the invention will become apparent from the following description of one of its embodiments, provided as a non-limiting example, with reference to the accompanying drawings.

In the drawings.

DETAILED DESCRIPTION OF THE DISCLOSURE

In the various figures, the same references designate identical or similar elements.

Figure 1:
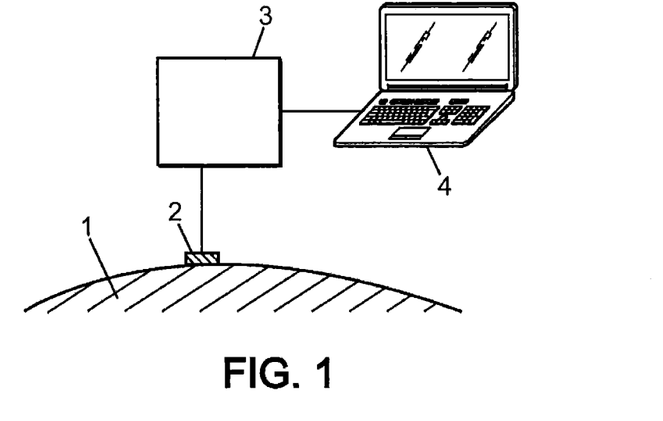
FIG. 1 is a schematic view of a device for implementing a method according to an embodiment of the invention.
Figure 2:
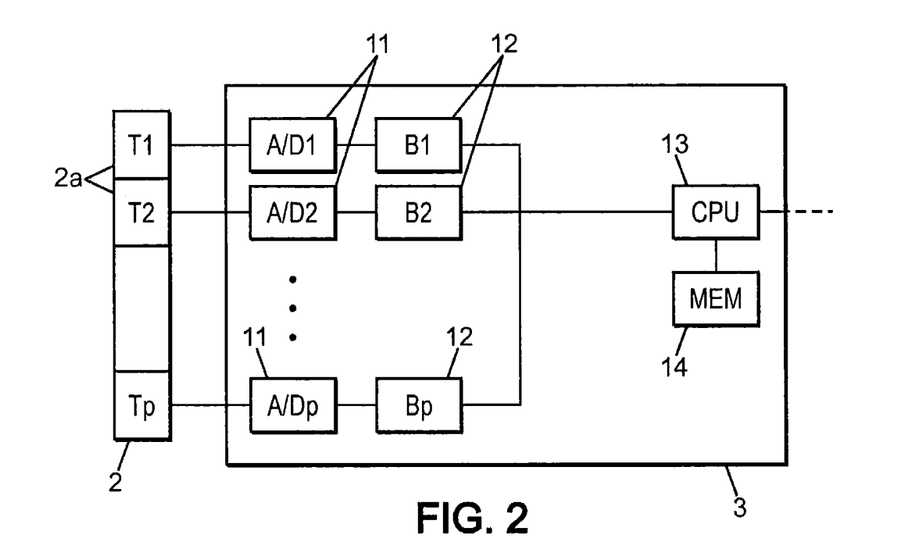
FIG. 2 is a block diagram of a portion of the device of FIG. 1.

FIGS. 1 and 2 show an example of a device for carrying out synthetic ultrasound imaging of a medium 1 to be imaged, for example tissues of a human or animal subject to be studied, by transmitting and receiving ultrasonic compression waves, for example at frequencies between 2 and 40 MHz, in particular between 2 and 10 MHz. The ultrasound image produced corresponds to a portion of the medium 1 which will be referred to here as the area of observation.

The transmission and reception of ultrasound waves can occur by means of an array 2 of p ultrasound transducers 2a ($T_1$-$T_n$), comprising for example several hundred transducers 2a (for example at least 100), the array 2 possibly being for example a linear array of transducers (1D array) adapted for creating a two-dimensional (2D) image or possibly being a two-dimensional array adapted for creating a three-dimensional (3D) image.

The imaging device also comprises, for example:

an electronic circuit 3 controlling the transducer array 2 and adapted to cause the transducer array to transmit ultrasound waves and to detect signals received by the transducer array;

a computer 4 or similar device for controlling the electronic circuit 3 and viewing the ultrasound images obtained from said detected signals.

As represented in FIG. 2, the electronic circuit 3 may comprise, for example:

p analog-to-digital converters 11 ($A/D_j$) individually connected to the p transducers $T_1$-$T_p$ of the transducer array 2, p buffers 12 ($B_j$) respectively connected to the p analog-to-digital converters 11, a processor 13 (CPU) communicating with the buffers 12 and computer 4 and adapted to process signals sent to the transducer array 2 and received from said transducer array, a memory 14 (MEM) connected to the processor 13.

The imaging device represented in FIGS. 1 and 2 is adapted for carrying out synthetic ultrasound imaging of the medium 1 as described in particular in document EP2101191.

Several main steps can be distinguished in this imaging method:
(a) a transmission/reception step
(b) a decoding step
(c) an image construction stage.

These steps will now be detailed. The transmission and decoding steps make use of encoding matrices $H_c$ and decoding matrices $H_d$, which are described above.

These encoding $H_c$ and decoding $H_d$ matrices are square matrices of order n, where n is a natural number at least equal to 2, preferably even, n for example being between 2 and 100, advantageously between 4 and 20.

The encoding matrices $H_c$ and decoding matrices $H_d$ are such that $Hc \cdot Hd = D$ where D is a diagonal matrix of order n in which all diagonal elements $d_{ii}$ are nonzero.

Preferably, D may be a diagonal matrix of order n in which all diagonal elements are positive, preferably greater than 1.

More preferably, matrix Hc may be proportional to a Hadamard matrix $H_n$ of order n, and matrix $H_d$ is the transpose of matrix Hc.

In other words:

$$H_c = \lambda \cdot H_n \quad (0)$$

and $$H_d = {}^tH_c \quad (0'),$$

where $\lambda$ is a non-zero constant.

Examples of Hadamard matrices $H_n$ are given below, for n=2 and n=4.

For n=2:

$$H_2 = \begin{bmatrix} 1 & 1 \\ 1 & -1 \end{bmatrix}$$

For n=2:

$$H_4 = \begin{bmatrix} 1 & 1 & 1 & 1 \\ 1 & -1 & 1 & -1 \\ 1 & 1 & -1 & -1 \\ 1 & -1 & -1 & 1 \end{bmatrix}.$$

In the case where the encoding matrix is a Hadamard matrix ($H_c = H_n$), the above diagonal matrix D is equal to n times the identity matrix (in other words all diagonal elements $d_{ii}$ of D are equal to n).

(a) Transmission/Reception Step
(a1) Transmission:

During the transmission/reception step, the processor 13 causes the transducer array 2 to successively transmit into a medium 1 a series of n incident acoustic waves $E_i(t)$, in particular ultrasound waves as described previously. The incident acoustic waves are generally pulses of less than a microsecond, typically about 1 to 10 cycles of the ultrasound wave at the center frequency. The bursts of incident waves may be separated from each other for example by about 50 to 200 microseconds.

Each of the incident acoustic waves is obtained by linearly combining n elemental incident waves $E0_i(t)$ which are either plane waves or diverging waves or waves focused at different points in space respectively having n different wavefronts.

As disclosed in EP2101191, these elemental waves are such that each would be transmitted by a plurality of transducers (preferably at least 10 transducers, and usually the p transducers of the array 2) in order to sweep the entire area to be imaged in the medium 1.

This linear combination occurs in a manner corresponding to the formula:

$$\vec{E}(t) = H_c \cdot \vec{E}0(t) \quad (1)$$

where:

$\vec{E}(t) = [E_i(t)]$ is a vector having the n incident waves as components, $\vec{E}0(t) = [E0_i(t)]$ is a vector having the n elemental incident waves as components.

The incident acoustic waves can be calculated in advance and stored for example in memory 14.

Each elemental incident wave is transmitted by a plurality of acoustic transducers of the array 2 of acoustic transducers and sweeps the entire area of observation.

Advantageously, each of the n incident acoustic waves $E_i(t)$ can be represented by a plurality of time signals $E_{ij}(t)$ representing said incident acoustic wave as respectively transmitted by the various transducers $T_j$ of said transducer array 2. Thus, $E_i(t)$ can be represented by a vector $E_i(t) = [E_{ij}(t)]$.

Similarly, each of the n elemental incident waves $E0_i(t)$ can be represented by a plurality of time signals $E0_{ij}(t)$ representing said elemental incident wave respectively at the different transducers $T_j$ of said transducer array 2. Thus $E0_i(t)$ can be represented by a vector $E0_i(t) = [E0_{ij}(t)]$.

One will note that for a same transmitted wave $E_i(t)$, therefore at constant i, the signals $E_{ij}(t)$ are all different from each other in their amplitude and temporal form, the encoding performed here being space-time encoding.

Each signal $E_{ij}(t)$ transmitted by transducer j is a linear combination of elemental signals $E_{ij}0(t)$, this linear combination being derived from the above formula (1)

$$\left( E_{ij}(t) = \sum_{k=1}^{n} H_{cik} \cdot E_{kj}0(t) \right).$$

As matrix Hc has non-zero coefficients, the above linear combination also has non-zero coefficients; in other words, the signal $E_{ij}(t)$ transmitted by each transducer j is a linear combination with non-zero coefficients (for example, +1 or −1 in the case of the Hadamard matrix) of all the elemental signals $E_{ij}0(t)$ corresponding to the different elemental waves i (n elemental waves in total).

The signals $E_{ij}0(t)$ from one transducer j to another also differ in their temporal form, this being necessary to obtain the desired shapes of the elemental waves.

In addition, the various components $E_{ij}0(t)$ are non-zero signals, so that the linear combination is effective and each signal $E_{ij}(t)$ is different from signal $E_{ij}0(t)$.

Figure 3:
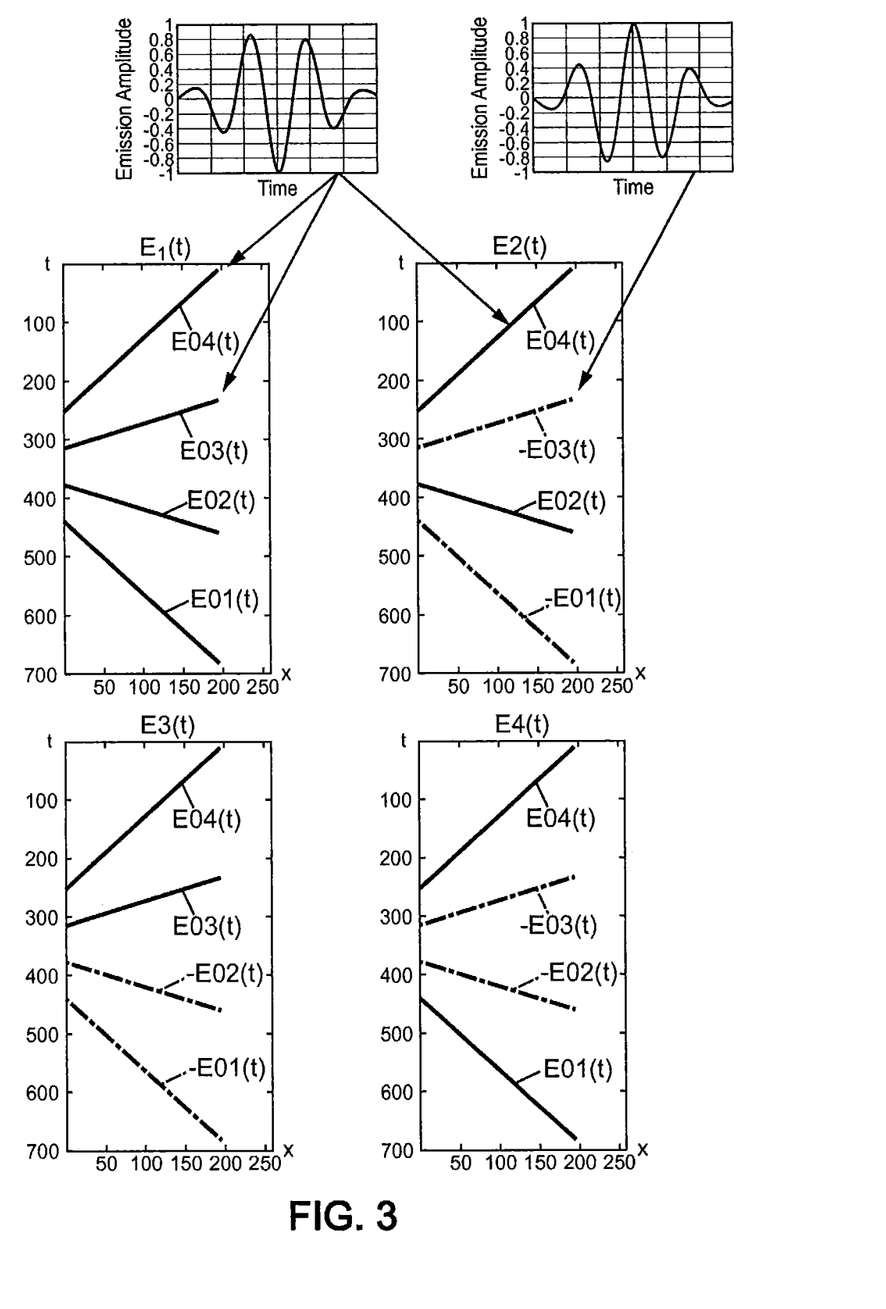
FIG. 3 is a series of timing diagrams showing the component elemental incident waves of the different incident acoustic waves that are successively transmitted in order to create a synthetic image.

FIG. 3 illustrates a special case where n=4, in which the incident acoustic waves $E_i(t)$ are linear combinations of four elemental incident waves which are plane waves $E0_i(t)$ of different inclinations, the wavefronts being represented along the X axis parallel to the transducer array and as a function of time t. In this example, the encoding matrix used is the abovementioned Hadamard matrix $H_4$.

Plane waves assigned a linear coefficient −1 (−E0$_i$(t)) are represented by phantom lines and plane waves assigned a linear coefficient +1 (+E0$_i$(t)) are represented by solid lines. As shown in the top detail views of FIG. 3 for waves E$_1$(t) and E$_2$(t), the waveforms of the elemental incident waves E0$_i$(t) can be damped sinusoids lasting for example about 3 cycles, the plane waves assigned linear coefficient −1 (−E0$_i$(t)) simply having an opposite waveform to E0$_i$(t).

(a2) Reception:

Each of the incident acoustic waves E$_i$(t) propagates through the medium 1 which returns a corresponding reverberated wave R$_i$(t). Before transmitting the next incident acoustic wave, the transducer array 2 detects the reverberated wave R$_i$(t) which is then transmitted to the processor 13 and stored in memory 14.

The reverberated wave R$_i$(t) is stored as a plurality of time signals R$_{ij}$(t) representing said reverberated wave as respectively detected by the various transducers T$_j$ of the transducer array 2. Thus, R$_i$(t) can be represented by a vector R$_i$(t)=[R$_{ij}$(t)].

(b) Decoding Step

After transmitting n incident acoustic waves E$_i$(t) and receiving n reverberated waves R$_i$(t), the processor 13 performs a decoding step in which n elemental reverberated waves R0$_i$(t) are determined by linearly combining the detected n reverberated waves R$_i$(t), corresponding to the formula:

$$\vec{R}0(t) = H_d \cdot \vec{R}(t) \quad (2)$$

where:

$\vec{R}(t)=[R_i(t)]$ is a vector having the n reverberated waves as components, $\vec{R}0(t)=[R0_i(t)]$ is a vector having the n elemental reverberated waves as components.

The elemental reverberated waves R0$_i$(t) are determined in the form of a plurality of time signals R0$_{ij}$(t) representative of said elemental reverberated wave at different transducers T$_j$ of the transducer array 2. Thus, R0$_i$(t) can be represented by a vector R0$_i$(t)=[R0$_{ij}$(t)], or more commonly by a matrix that is exactly R0$_i$(t)=[R0$_{ijk}$(t$_k$)] after time sampling at K moments t$_k$.

(c) Image Construction Step

After the decoding step (b), the processor 13 carries out an image construction step, in which a synthetic image is created from the n elemental reverberated waves R0$_i$(t), for example as taught in document EP2101191 or in the article by Montaldo et al. entitled "Coherent plane-wave compounding for very high frame rate ultrasonography and transient elastography" (IEEE Trans Ultrason Ferroelectr Freq Control 2009 March; 56(3): 489-506).

The elemental reverberated waves R0$_i$(t), generally presented in matrix form R0$_i$(t)=[R0$_{ijk}$(t$_k$)] as previously indicated, constitute the matrices of initial raw data (or "RF raw data") of the methods described in the aforementioned documents. Specifically, from the n matrices R0$_i$(t) of RF raw data, the processor 13 calculates coherent synthetic RF data matrices, respectively at M points P$_m$(x,z) of the medium to be imaged 1 (referred to as virtual focal points), m being an integer between 1 and M, x being the abscissa of point P$_m$ on an X axis parallel to the transducer array 2 in the case of a linear transducer array 2 (x being replaced by x,y in the case of a two-dimensional array 2), and z is the depth in the medium 1, along a Z axis perpendicular to the X axis. Each of these M matrices of coherent synthetic RF data comprises p time signals RFcoherent$_{m,j}$(t) corresponding to the signals that would be respectively detected by the p transducers T$_j$ if the transducers transmit an incident wave focused at point P$_m$.

The matrices of coherent RF data may be obtained for example by assuming a homogeneous propagation velocity c throughout the medium 1 for ultrasonic compression waves, according to the principle explained in particular in document EP2101191 or in the article by Montaldo et al. entitled "Coherent plane-wave compounding for very high frame rate ultrasonography and transient elastography" (IEEE Trans Ultrason Ferroelectr Freq Control 2009 March; 56(3): 489-506).

As the direction of propagation of the plane wave corresponding to each elemental incident wave E0$_i$(t) is known, and the propagation velocity c is known, the processor 13 can calculate for each point P$_m$ the propagation time $\tau_{ec}$(i,m) of the elemental incident wave i to point P$_m$, and the propagation time $\tau_{rec}$(i,m,j) of the elemental reverberated wave from point P$_m$ to transducer T$_j$, therefore the total time of the round trip $\tau$(i,m,j)=$\tau_{ec}$(i,P$_m$)+$\tau_{rec}$(i,P$_m$,j), The spatially coherent signal for transducer Tj, corresponding to the virtual focal point P$_m$, is then calculated using the formula:

$$RFcoherent_{mj}(t) = \sum_i B(i) RFraw_{ij}(, \tau(i, m, j)) \quad (3)$$

where B(i) is a function for weighting the contribution of each elemental incident wave i (it is possible for the coefficients B(i) to all be equal to 1).

The coherent data matrices RFcoherent$_{mj}$ may then possibly be refined by correcting the effects of aberrations in the medium 1, for example as explained in the aforementioned documents EP2101191 or Montaldo et al.

The processor 13 can then perform conventional reception beamforming to obtain an ultrasound image as explained in the aforementioned documents EP2101191 or Montaldo et al., and/or apply more elaborate processing (calculating a Doppler or color Doppler image for example), these being known per se.

The image construction method is similar when the transducer array 2 is two-dimensional, or when the elemental incident waves and elemental reverberated waves are diverging.

In all cases, the resulting image exhibits a clearly increased resolution in comparison to an image obtained by conventional synthetic imaging via transmission of plane waves (as described by the above documents EP2101191 or Montaldo et al).

Figure 4A:
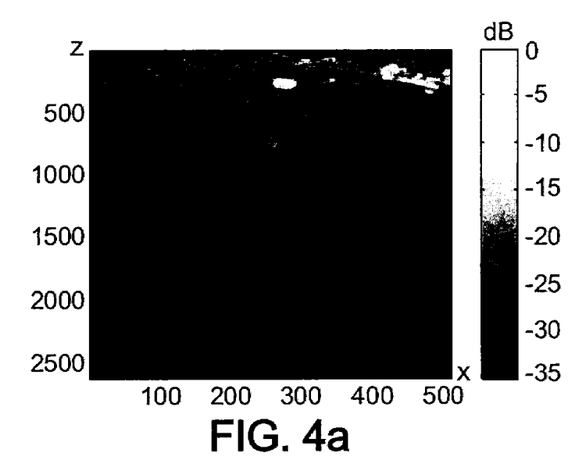
FIGS. 4a to 4d are ultrafast Doppler images showing the vasculature of a brain, 4a and 4c being obtained in two different planes by synthetic imaging without the present invention, and FIGS. 4b and 4d being respectively obtained in the same planes by synthetic imaging with the present invention.
Figure 4B:
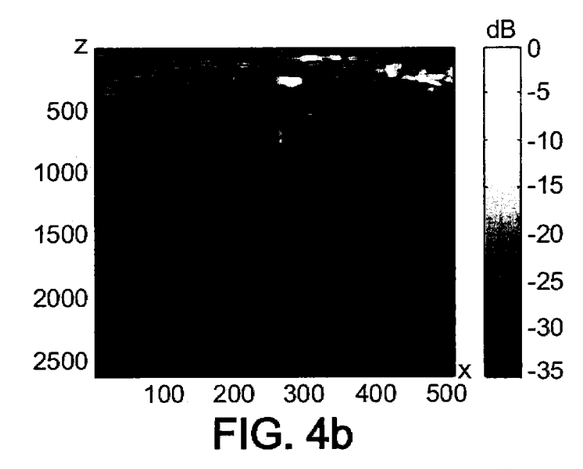
Figure 4C:
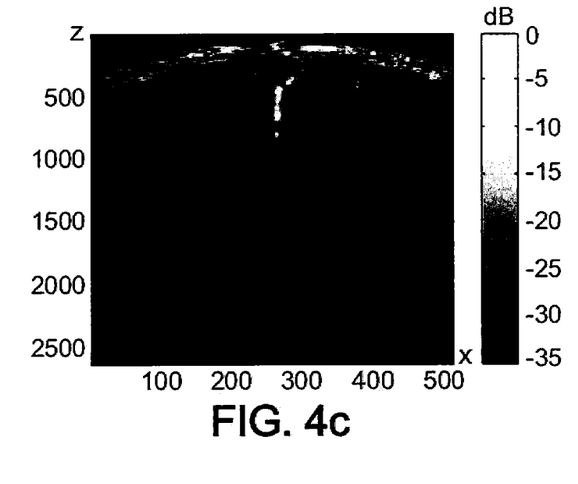
Figure 4D:
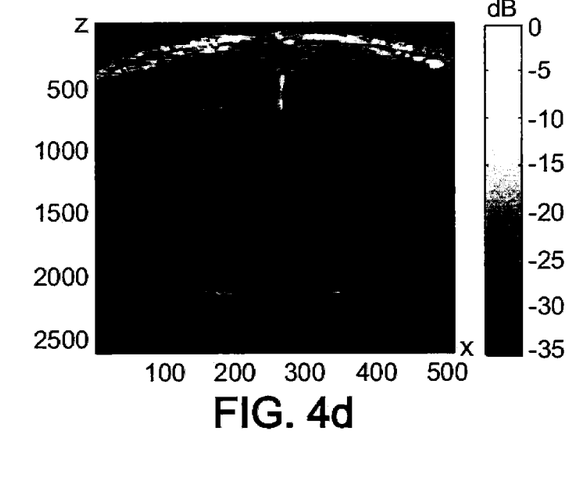

Thus, FIGS. 4a and 4c of ultrafast Doppler images show vascularization of a rat brain, carried out in two different planes by synthetic imaging with transmission of plane waves (without the present invention), while FIGS. 4b and 4d are respectively carried out in the same planes using synthetic imaging with the present invention: the clearly increased resolution of the images of FIGS. 4b and 4d is visible to the eye.

Figure 5A:
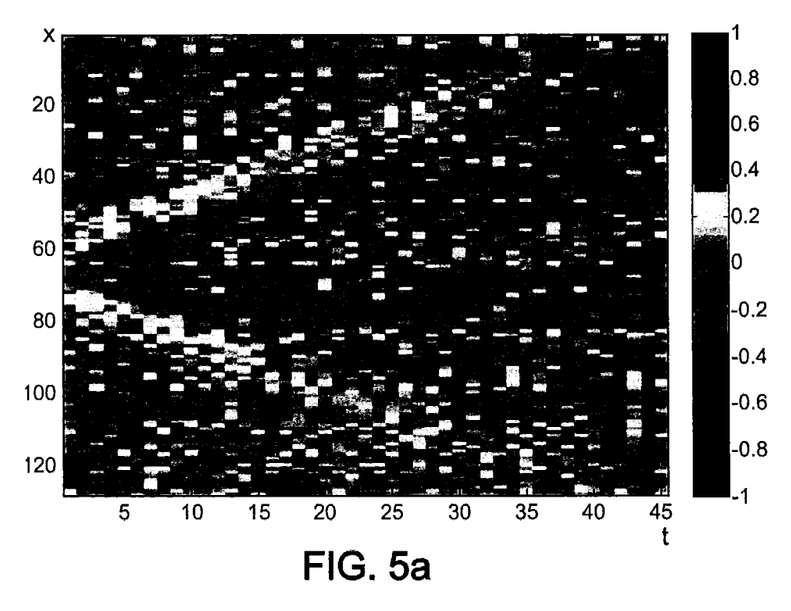
FIGS. 5a and 5b are elastographic images showing the propagation of a shear wave in human tissue, obtained by synthetic imaging with and without the invention.
Figure 5B:
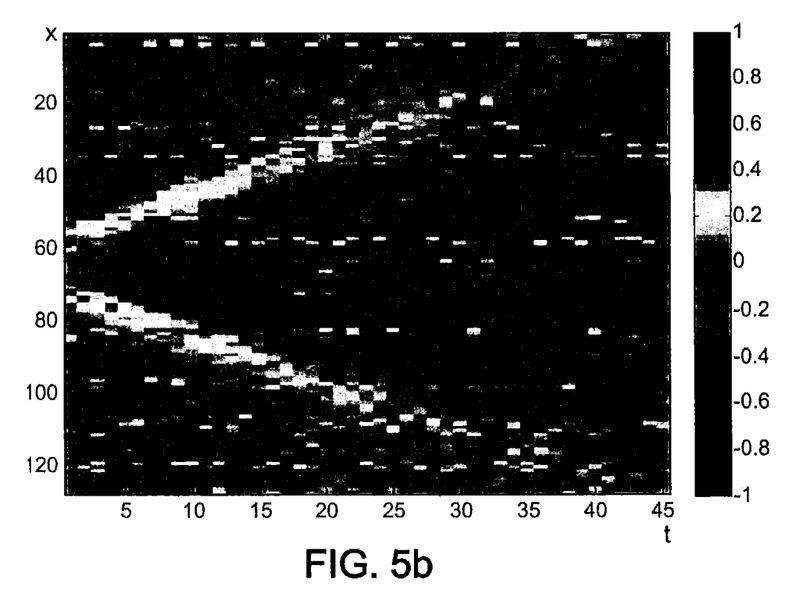

Similarly, FIGS. 5a and 5b are elastographic images showing the propagation of a shear wave in human tissue, obtained by synthetic imaging respectively without and with the invention: the superior resolution of the image of FIG. 5b is visible to the eye.

The invention claimed is:

1. An acoustic imaging method comprising the following steps:

a transmission/reception step during which:
an array of acoustic transducers successively transmits a series of n incident acoustic waves Ei(t) in an area of observation that is part of a medium to be imaged, and the array of acoustic transducers detects n reverberated waves Ri(t) which are respectively reverberated by the medium to be imaged following the transmission of the n incident acoustic waves Eirt), n being a natural number at least equal to 2, wherein:
each of said n incident acoustic waves is obtained by linearly combining n elemental incident waves E0i(t) in a manner corresponding to the formula:

$$E(t) = H_c \cdot E0(t) \qquad (1)$$

where: H, is a square matrix of order n,
E(t)=[E(t)] is a vector having the n incident acoustic waves as components,
E0(t)=[E01(t)] is a vector having the n elemental incident waves E0,(t) as components, and
wherein: said elemental incident waves are plane waves or diverging waves or waves focused at different points in space respectively having n different wave fronts,
each elemental incident wave E0$i$(t) of said n elemental incident waves is transmitted by a plurality of transducers of the array (2) of acoustic transducers and sweeps the entire area of observation,
said plurality of transducers comprises a number of transducers superior or equal to 10 and strictly superior to the number n of incident acoustic waves transmitted by said plurality of transducers;
wherein each of said incident acoustic waves Ei(t) is represented by a plurality of time signals Ei;(t), each time signal representing said acoustic wave at a transducer that is part of said transducer array, said time signals Ei1(t) being all different from each other in their amplitude and temporal form,
a decoding step during which n elemental reverberated waves R0$i$(t) are determined by linearly combining the n reverberated waves Ri(t) detected, corresponding to the formula:

$$R0(t) = H_d R(t) \qquad (2)$$

where:
Hd is a square matrix of order n, the matrices H, and Hd being such that $H_c \cdot H_d = D$ where D is a diagonal matrix of order n in which all diagonal elements dii are non-zero,
R(t)=[R1$i$(t)] is a vector having the n reverberated waves as components,
RO(t)=[R01(t)] is a vector having the n elemental reverberated waves as components;
an image construction step during which a synthetic image is produced from the n elemental reverberated waves ROi(t).

2. The method according to claim 1, wherein the matrices $H_c$ and $H_d$ are such that $H_c \cdot H_d = D$, where D is a diagonal matrix of order n in which all diagonal elements $d_{ii}$ are greater than 1.

3. The method according to claim 1, wherein n is an even non-zero natural number.

4. The method according to claim 1, wherein matrix $H_c$ is a Hadamard matrix of order n and matrix $H_d$ is the transpose of matrix $H_c$.

5. The method according to claim 1, wherein the medium to be imaged comprises living human or animal biological tissue.

6. The method according to claim 1, wherein said number of transducers of said plurality of transducers is superior or equal to 100 and said number n of incident acoustic waves transmitted is comprised between 4 and 20.

7. An acoustic imaging device, comprising: a transmission means adapted for successively transmitting a series of n incident acoustic waves Ei(t) in an area of observation within a medium to be imaged, by means of an array of acoustic transducers, wherein:
each of said n incident acoustic waves is obtained by linearly combining n elemental incident waves E0$i$(t) in a manner corresponding to the formula:

$$E(t) = H_c \cdot E0(t) \qquad (1)$$

where:
H. is a square matrix of order n,
E(t)=[Ei(t)] is a vector having the n incident acoustic waves as components,
E0(t)=[E01 (t)] is a vector having the n elemental incident waves E0$i$t as components, and
wherein: said elemental incident waves E0$i$(t) are plane waves or diverging waves or waves focused at different points in space respectively having n different wave fronts,
each elemental incident wave E0$i$(t) of said n elemental incident waves is transmitted by a plurality of acoustic transducers of the array and sweeps the entire area of observation, and
said plurality of transducers comprises a number of transducers superior or equal to 10 and strictly superior to the number n of incident acoustic waves transmitted by said plurality of transducers;
reception means adapted for successive detection by the array of acoustic transducers of n reverberated waves Ri(t) which are respectively reverberated by the medium to be imaged following the transmission of the n incident waves Ei(t);
wherein each of said incident acoustic waves Ei(t) is represented by a plurality of time signals Ei;(t), each time signal representing said acoustic wave at a transducer that is part of said transducer array, said time signals Ei1 (t) being all different from each other in their amplitude and temporal form,
decoding means adapted for determining n elemental reverberated waves R0$i$(t) by linearly combining the detected n reverberated waves Ri(t), in a manner corresponding to the formula:

$$R0(t) = H_d R(t) \qquad (2)$$

where:
Hd is a square matrix of order n, matrices H, and Hd being such that $H_c \cdot H_d = D$ where D is a diagonal matrix of order n in which all diagonal elements dii are non-zero,
R(t)=[R1$i$(t)] is a vector having the n reverberated waves as components,
RO(t)=[R01(t)] is a vector having the n elemental reverberated waves as components;
image construction means adapted for creating a synthetic image from the n elemental reverberated waves ROi(t).

8. The acoustic imaging device according to claim 7, wherein said number of transducers of said plurality of transducers is superior or equal to 100 and said number n of incident acoustic waves transmitted is comprised between 4 and 20.

* * * * *